United States Patent
Hayashi

(10) Patent No.: US 6,403,560 B1
(45) Date of Patent: Jun. 11, 2002

(54) IMMUNOPOTENTIATOR AND METHOD FOR PREPARING THE SAME

(75) Inventor: Seiji Hayashi, Ena-gun (JP)

(73) Assignee: Adaptgen Pharmaceutical Co., Ltd., Gifu (JP)

( * ) Notice: Subject to any disclaimer, the term of this patent is extended or adjusted under 35 U.S.C. 154(b) by 0 days.

(21) Appl. No.: 09/685,135

(22) Filed: Oct. 11, 2000

(30) Foreign Application Priority Data

Jun. 20, 2000 (JP) ........................................ 2000-185112

(51) Int. Cl.[7] ........................... A61K 38/16; C12P 21/09
(52) U.S. Cl. ........................... 514/12; 435/70.1; 514/12; 514/21
(58) Field of Search ..................... 514/21, 12; 435/70.1

(56) References Cited

FOREIGN PATENT DOCUMENTS

| CN | 1063692 | 8/1992 |
|---|---|---|
| JP | 58-37001 | 3/1983 |
| JP | 59-116204 | 7/1984 |
| WO | WO 98/52605 | 11/1998 |
| WO | WO 00/12122 | 3/2000 |
| WO | WO 00 12122 | * 3/2000 |

OTHER PUBLICATIONS

Uhlin et al., "Enhanced Humoral Immune Response in Rats by Hyaluronic Acid", International Journal of Immunopharmacology, vol. 4, No. 6, 1982 (pp. 529–532).

* cited by examiner

Primary Examiner—Geetha P. Bansal
Assistant Examiner—Natalie Davis
(74) Attorney, Agent, or Firm—Oliff & Berridge, PLC

(57) ABSTRACT

An immunopotentiator containing peptide and hyaluronic acid extracted from chicken comb or mammalian skin or organ is provided, the immunopotentiator having a great immunopotentiation effect on biological organisms; additionally, a method for preparing the immunopotentiator is provided, comprising immersing and swelling chicken comb or mammalian skin or mammalian organ in a minced state and hydrolyzing the protein in the mincemeat to peptide.

1 Claim, 3 Drawing Sheets

Tumor on right side (dosed side)

Tumor on left side (non-dosed side)

Effect of dosing into Meth-A fibreosarcoma (solid tumor) in BALB/c mouse
Significant difference from control group
(* $p > 0.05$  ** $p < 0.01$)

IMMUNOPOTENTIATOR AND METHOD FOR PREPARING THE SAME

BACKGROUND OF THE INVENTION

This application No. 09/685,135, filed Oct. 11, 2002, claims priority to foreign application JAPAN 2000-185112, filed Jun. 20, 2000.

1. Field of the Invention

The present invention relates to an immunopotentiator enhancing the immunopotency of biological organisms and a method for preparing the same.

2. Description of the Related Art

Biological organisms essentially have immunopotency, but the intensity of the immunopotency varies, depending on individual differences and condition at a certain time. Alternatively, the present inventors have made investigations about hyaluronic acid for a long time and have made a finding that simultaneous administration of hyaluronic acid and peptide can enhance the immune action of biological organisms.

SUMMARY OF THE INVENTION

The present invention has been achieved on the basis of the finding and has an object to provide an immunopotentiator and a method for preparing the same, which can enhance the immunopotency of biological organisms.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an immunopotentiator contains peptide and hyaluronic acid as effective components.

In a second aspect of the invention, preferably, the peptide and hyaluronic acid are simultaneously extracted from chicken comb or mammalian skin or mammalian organ.

In a third aspect of the invention, the immunopotentiator according to the claims 1 and 2 can be prepared by immersing and swelling chicken comb or mammalian skin or mammalian organ in a minced state and hydrolyzing the protein in the mincemeat to peptide.

According to the present invention, the inventive immunopotentiator exerts great immunopotentiation effect in biological organisms. Additionally, because chicken comb contains protein and hyaluronic acid abundantly, both the protein and hyaluronic acid are simultaneously extracted from the same source of chicken comb, satisfactorily. Compared with a process of separately extracting peptide and hyaluronic acid and mixing them together, the present process never includes any useless step but is highly safe because chicken comb is used as a raw material.

DETAILED DESCRIPTION OF THE INVENTION

The method for preparing the immunopotentiator of the invention from a raw material for example chicken comb is now described specifically.

A. Chicken comb is generally in a frozen state, thus chickencomb is firstly thawed. The thawed comb is then rinsed with distilled water dissolving therein 0.1% chlorine. Then, the rinsed comb is minced with a mincing machine.

B. The mincemeat is placed in a reaction oven, followed by addition of caustic soda; and the resulting mixture is left to stand for about 15 hours. In this manner, the mincemeat is sufficiently swollen.

C. Hydrochloric acid is added to the swollen mincemeat to final pH 7–8; protease as the enzyme for decomposing protein is added at 0.5% to the resulting mincemeat for enzymatic decomposition (hydrolysis) for 2.5 hours; then, the mixture is preliminarily filtered through a 50-mesh screen; to the filtrate is additionally added celite as a filtration auxiliary agent for prevention of clogging, followed by second filtration through a 10-micron filter paper.

D. Active charcoal is added at 0.5% to the filtrate. The filtrate is deodorized and decolored with the active charcoal, which is then filtered through a 1-micron filter paper to remove the active charcoal.

After the completion of the process D, the resulting filtrate corresponds to the immunopotentiator containing peptide and hyaluronic acid as the effective components. The immunopotentiator can be given orally or parenterally at appropriate dosage forms (for example, liquids, granules, tablets, capsules, etc.) suitable for individual dosage recipes. Herein, mammalian skin or mammalian organs are also used as raw materials for such preparation by the method described above.

An immunopotentiation test using the immunopotentiator of the invention is now described below.

[Cellular Immunopotentiation Test 1]

Figure 1:
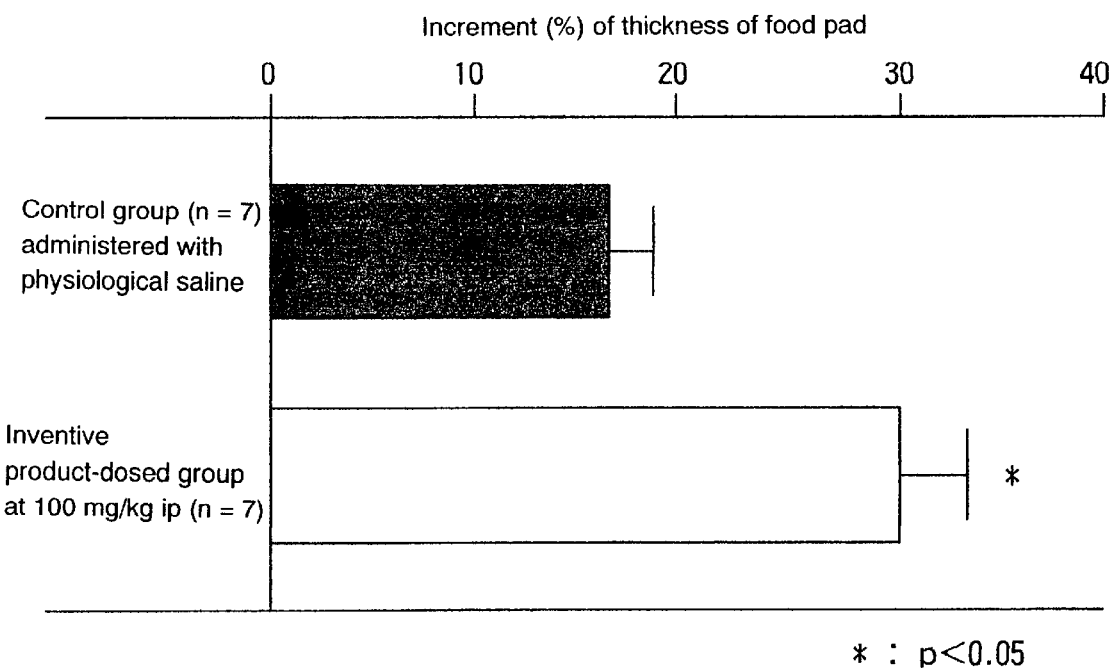
FIG. 1 shows bar graphs depicting test results.

40 $\mu$l of $2.5\times10^8$ cells/ml sheep red blood cell (SRBC) was subcutaneously injected to left pads of ICR mice (age 6 to 8 weeks; male; 7 animals per group) by using a microsyringe, for antigen sensitization. Six days after sensitization, 40 $\mu$l of $2.5\times10^9$ cells/ml SRBC was subcutaneously injected to the right pads; 24 hours later, the size of edema on the right pads was measured with a dial thickness gauge (0.01 mm). The immunopotentiator of the invention was intraperitoneally dosed at 100 mg/kg one hour prior to the antigen SRBC sensitization. To a control group, physiological saline was dosed at the same dose. The results are shown in the graphs of FIG. 1.

[Test Results]

In the control mouse group, the swelling degree was at 16.2±2.4%, while in the inventive immunopotentiator-dosed group, the swelling degree was at 30.1±3.5%. The degree of swelling was increased with a significant difference (p<0.05). In the test, a delayed dermal reaction was examined; T lymphocyte sensitized with the preliminarily injected red blood cell was allowed to react with the antigen (red blood cell boosted at a second time) 6 days later, to consequently release lymphokine, so that macrophage and white blood cell were activated for infiltration, leading to the emergence of edema. In the test, strong swelling was apparently observed in the inventive immunopotentiator-dosed group. Thus, it is indicated that cellular immunity was enhanced.

[Cellular Immunopotentiation Test 2: Oral Dosing]

Figure 2:
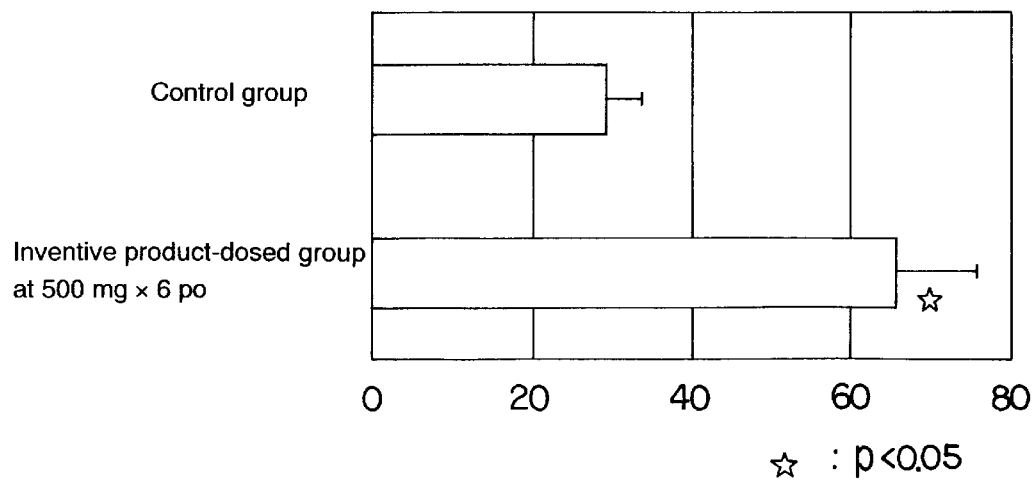
FIG. 2 shows bar graphs depicting test results.

40 $\mu$l of $4.0\times10^8$ cells/ml sheep red blood cell (SRBC) was subcutaneously injected to left pads of ICR mice (age 6 to 8 weeks; male; 7 animals per group) by using a microsyringe, for antigen sensitization. Four days after the sensitization, 40 μl of 4.0×10$^9$ cells/ml SRBC was subcutaneously injected to the right pads; 24 hours later, the size of edema on the right pads was measured with a dial thickness gauge (0.01 mm). The immunopotentiator of the invention was orally dosed at 500 mg/kg continuously six times, prior to the sensitization. To a control group, alternatively, physiological saline was dosed at the same dose. The results are shown in the graphs of FIG. 2.

[Test Results]

In the control mouse group, the swelling degree was at 29.3±4.5%, while in the inventive immunopotentiator-dosed group, the swelling degree was at 65.5±10.3%. The degree of swelling was increased with a significant difference ($p<0.05$). Thus, immunopotentiation via oral dosing was observed at the test.

[Somatic Immunopotentiation Test]

So as to examine somatic immunity, the enhancement of the generation of immunoglobulin (IgM, IgG) was confirmed.

[Test Method]

The inventive immunopotentiator was intraperitoneally dosed at 300 mg/kg in ICR mice (of body weight about 30 g). One hour later, the mice were sensitized with % SRBC at 0.4 ml/kg body weight. Six days later, blood was drawn, from which serum was separated to recover anti-serum; aggregation was confirmed on a 96-well plate to determine the antibody titer. To the mice in a control group, physiological saline in place of the inventive immunopotentiator was dosed, to recover the sera similarly. The results are shown in Table 1.

TABLE 1

Somatic immunopotentiation test

| | | Aggregation titer | |
| --- | --- | --- | --- |
| | Dose (mg/kg) | IgM | IgG |
| Dose group | 300 | 12.0 ± 0* | 11.5 ± 0.2* |
| Control group | 0 | 8.2 ± 0.3 | 8.1 ± 0.2 |

*difference at a 0.05-% level of significance.

[Test Results]

Compared with the control group, both the antibody titers of IgM and IgG in the mice in the inventive immunopotentiator-dosed group were significantly enhanced ($p<0.05$). In the test, the antibody titer was distinctively elevated in the inventive immunopotentiator-dosed group, which indicates enhancement of antibody generation potency.

[Anti-tumor Test]

Figure 3:
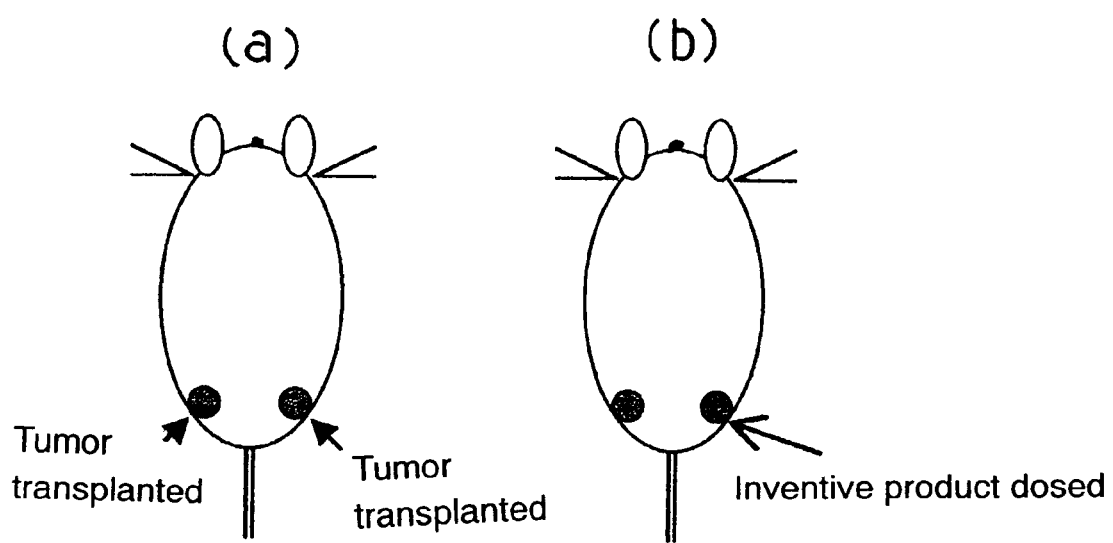
FIGS. 3(a) and (b) show plain views depicting tumor-transplanted sites and the inventive immunopotentiator-dosed sites in mice.
Figure 4:
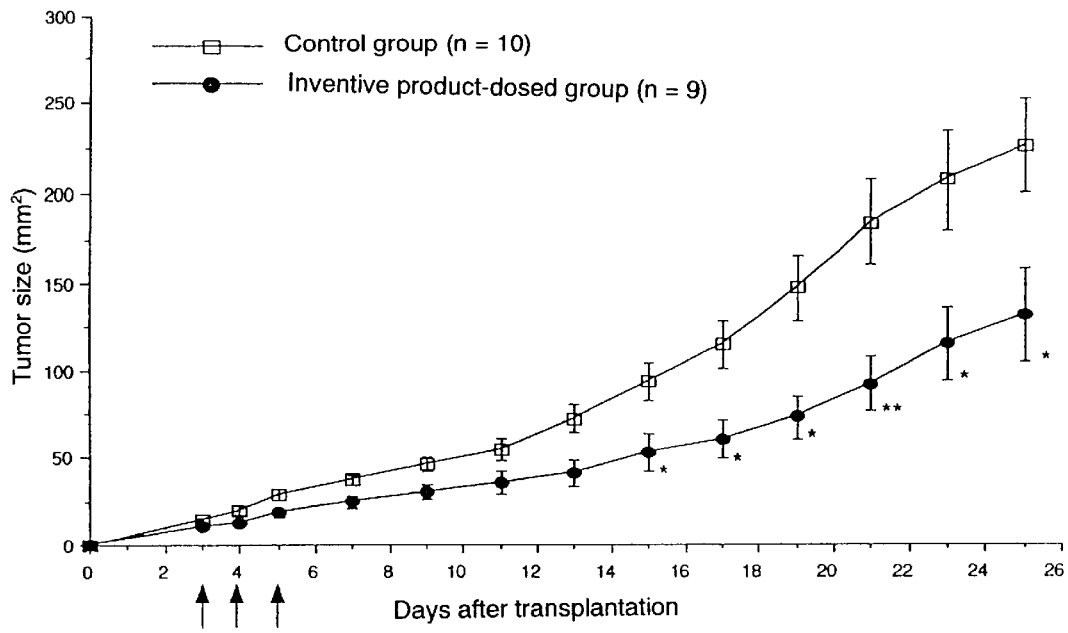
FIG. 4 shows graphs depicting test results.
Figure 4:
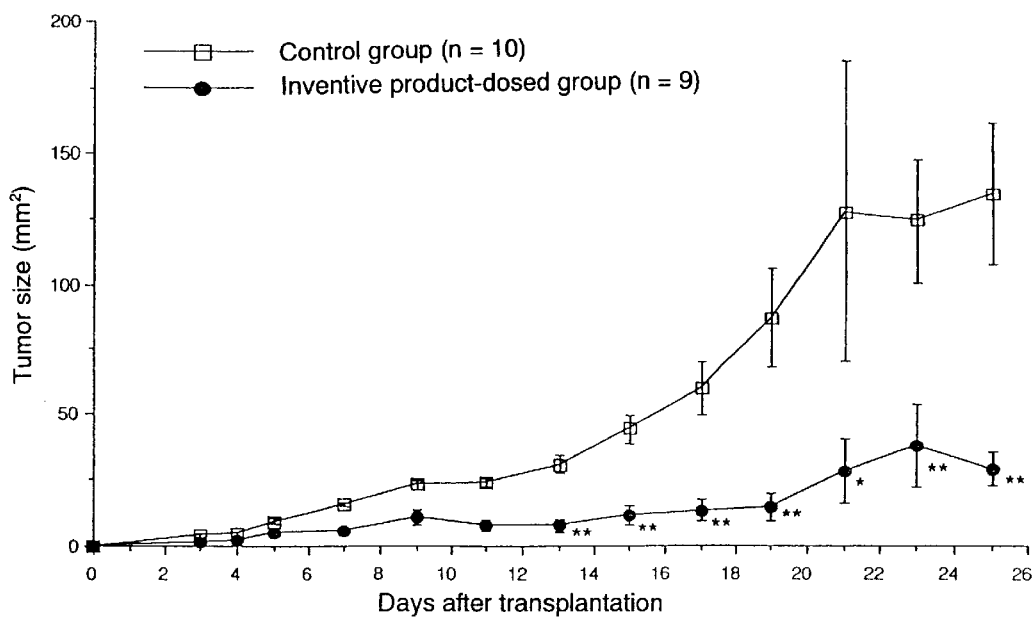

Meth-A fibreosarcoma was transplanted subcutaneously at 1×10$^6$ cells and 2×10$^5$ cells in the right lower abdominal part and left lower abdominal part, respectively, of BALB/c mouse (age 7 weeks), as shown in FIG. 3(a). The inventive immunopotentiator was dissolved in physiological saline and then administered at a dose of 1 mg/kg/0.1 ml/mouse into only the right tumor transplanted, three times continuously on days 3, 4 and 5 after tumor transplantation. The long diameter and short diameter of the right and left tumors were measured over time; the size of the tumors was compared with the size in the control group dosed with physiological saline. The results are shown in Table 2 and the graphs of FIG. 4.

TABLE 2

Test results of the dosing of the inventive immunopotentiator into Meth-A fibreosarcoma (solid tumor) in BALB/c mouse

| | Dose in tumor (mg/animal) × days | Dosing period (days) | Animal number (animals) | Mean tumor weight (g ± SE) | Tumor suppression ratio (%) |
| --- | --- | --- | --- | --- | --- |
| Dosing group | 1 × 3 | 3 to 5 | 9 | 0.589 ± 0.231 | 52.5 |
| Control group | 0 × 3 | 3 to 5 | 10 | 1.240 ± 0.329 | — |

*Tumor cell (1 × 10$^6$) was subcutaneously transplanted (on day 0).
*The inventive immunopotentiator was dosed into the tumor on the right side on days 3, 4 and 5.

Although the inventive immunopotentiator was dosed into only the tumor on the right side, it was observed that the tumor growth was suppressed on the tumors on both the right and left sides. This indicates that the anti-tumor action of the inventive immunopotentiator includes a direct suppressive action and an action suppressing remote tumor. Thus, it is indicated that host immune function is possibly activated in a certain mode.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated.

For example, chicken comb is listed as a raw material in the examples, but animal eyeballs and organs such as aorta are also satisfactorily used. Additionally, hydrolysis procedures are not specifically limited. Other than enzymatic decomposition with protease, alkali hydrolysis is also satisfactory.

It is intended that the scope of the invention be defined by the claims appended hereto, and their equivalents.

What is claimed is:

1. A method of enhancing immunopotency of biological organisms, comprising:

extracting hyaluronic acid together with a protein from chicken comb, mammalian skin or mammalian organ;

deriving hyaluronic acid and peptide mixture from the hyaluronic acid and protein mixture;

forming an immunopotentiator from the hyaluronic acid and peptide mixture; and orally administering the immunopotentiator to enhance immunopotency.

* * * * *